(12) United States Patent
Kurzrock et al.

(10) Patent No.: US 11,793,920 B2
(45) Date of Patent: Oct. 24, 2023

(54) LIQUID RECEPTACLE FOR A PUMPING APPARATUS

(71) Applicant: Moxxly LLC, Wiimington, DE (US)

(72) Inventors: Jacob Kurzrock, San Francisco, CA (US); Camille I. Henrot, San Francisco, CA (US); Gabrielle Guthrie, San Francisco, CA (US); Santhi Analytis, San Francisco, CA (US); Cara Delzer, San Francisco, CA (US)

(73) Assignee: Moxxly, LLC, Wilmington, DE (US)

( * ) Notice: Subject to any disclaimer, the term of this patent is extended or adjusted under 35 U.S.C. 154(b) by 1062 days.

(21) Appl. No.: 16/397,913

(22) Filed: Apr. 29, 2019

(65) Prior Publication Data
US 2019/0328944 A1    Oct. 31, 2019

Related U.S. Application Data (60) Provisional application No. 62/663,735, filed on Apr. 27, 2018.

(51) Int. Cl.
| | |
|---|---|
| *A61M 1/00* | (2006.01) |
| *A61J 1/10* | (2006.01) |
| *A61M 1/06* | (2006.01) |
| *A61J 1/18* | (2023.01) |
| *A61M 39/24* | (2006.01) |
| *A61J 1/14* | (2023.01) |
| *A61J 1/20* | (2006.01) |
| *A61M 39/10* | (2006.01) |

(52) U.S. Cl.
CPC .................. *A61M 1/60* (2021.05); *A61J 1/10* (2013.01); *A61J 1/1412* (2013.01); *A61J 1/1475* (2013.01); *A61J 1/18* (2013.01); *A61J 1/2024* (2015.05); *A61J 1/2048* (2015.05); *A61M 1/062* (2014.02); *A61M 39/24* (2013.01); *A61J 2205/20* (2013.01); *A61M 2039/1038* (2013.01)

(58) Field of Classification Search
CPC .................. A61M 1/062; A61M 39/24; A61M 2039/1038; A61M 1/0001; A61M 1/69; A61J 1/10; A61J 1/1412; A61J 1/1475; A61J 1/18; A61J 1/2024; A61J 1/2048; A61J 2205/20
See application file for complete search history.

(56) References Cited

U.S. PATENT DOCUMENTS

| | | | |
|---|---|---|---|
| 6,576,278 B1 * | 6/2003 | Sprehe | A61J 9/001 426/117 |
| 2002/0156419 A1 * | 10/2002 | Silver | A61M 1/06 604/74 |
| 2017/0172852 A1 * | 6/2017 | McBean | A61M 1/062 |

FOREIGN PATENT DOCUMENTS

WO    WO-2008038054 A2 *    4/2008    ............ A61J 11/008

* cited by examiner

*Primary Examiner* — Amber R Stiles
(74) *Attorney, Agent, or Firm* — Travis Banta; Loyal IP Law, PLLC (57) ABSTRACT

Disclosed herein are methods, systems, and devices for collecting a fluid for use in connection with a fluid pumping device such as a breast pump. A fluid collection receptacle includes a rigid connector attached to the fluid collection receptacle. The rigid connector is connectable to a breast pump manifold. The fluid collection receptacle further includes a liquid tight seal in the fluid collection receptacle. The fluid collection receptacle may be constructed of a flexible plastic.

17 Claims, 8 Drawing Sheets

LIQUID RECEPTACLE FOR A PUMPING APPARATUS

CROSS-REFERENCE TO RELATED APPLICATIONS

This application claims the benefit of U.S. Provisional Application No. 62/663,735, filed Apr. 27, 2018, which is incorporated herein by reference in its entirety, including but not limited to those portions that specifically appear hereinafter, the incorporation by reference being made with the following exception: In the event that any portion of the above-referenced provisional application is inconsistent with this application, this application supersedes said above-referenced provisional application.

TECHNICAL FIELD

The disclosure relates generally to systems, methods, and devices for a liquid receptacle and particularly relates to systems, methods, and devices for a liquid receptacle configured to be used in connection with a pumping apparatus such as a breast pump.

BACKGROUND

The disclosure relates to systems, methods, and devices for a liquid receptacle for use in connection with an apparatus for pumping a liquid. Such liquid receptacles of the present disclosure may be configured for use in connection with a breast pump and may be configured to safely and hygienically store breastmilk during and after pumping.

Breast feeding an infant can be a rewarding experience for a mother and provide numerous health benefits to an infant. Many medical experts, including professionals in the field of pediatrics and obstetrics, recognize the benefits of breastmilk and recommend exclusive breastfeeding for at least the first six months of an infant's life. Breastmilk provides ideal nutrition for an infant and includes a mix of vitamins, protein, and fat necessary for the infant's growth. Additionally, breastmilk is more easily digested by an infant than commercially produced infant formulas. Breastmilk uniquely contains antibodies from the mother's immune system that help fortify the infant's immune system to fight off viruses and bacteria and reduce the infant's risk of experiencing asthma or allergies. Additionally, studies indicate that infants who ingest breastmilk exclusively for the first six months of life, without any commercially produced infant formula, experience fewer ear infections, respiratory illnesses, and hospitalizations or trips to a medical professional. Exclusive ingestion of breastmilk is additionally linked to higher IQ score in later childhood in some studies and infants who ingest breastmilk are likely to gain an ideal amount of weight.

However, some mothers may have difficulty nursing a new baby. Many mothers may have physical difficulties nursing an infant directly at her breast. Additionally, many mothers do not have the opportunity to exclusively nurse infants directly at her breast but still wish to exclusively provide infants with breastmilk nutrition. Breast pumps have been developed to assist such women in expressing milk by mechanical systems. A mother may collect milk expressed by a breast pump and immediately feed the milk to her infant or store it short-term or long-term for later use. Such breast pumps may further enable fathers or other friends or family members to feed the infant and bond with the infant in that manner. Additionally, breast pumps may enable a mother to express milk to be fed to, for example, a premature infant who cannot yet nurse directly at the mother's breast.

Conventional fluid collection receptacles for use in connection with a breast pump are not well suited for long term storage of milk. Conventional fluid collection receptacles include rigid bottles configured to be attached to a breast pump apparatus which are designed specifically for use with a breast pump apparatus, requiring sanitization before a subsequent pumping session, making these rigid bottles non-ideal for long term storage of milk. It may not also be feasible for a mother to sanitize such a bottle in, for example, a dishwasher on high heat before each breast pumping session. The bottle may collect viruses, bacteria, and other minerals that may be harmful to the infant when ingested with the expressed breast milk. Additionally, bottles consume significant storage space and are difficult to wash, dry, and store. Bottles are often not suitable for long-term storage of breastmilk in a freezer because the bottle itself may be constructed of a material that is not compatible with freezing temperatures. Additionally, the bottle consumes significant storage space in a freezer and it is very difficult and time-consuming to thaw the milk when needed. Further, bottles can be expensive and some parents may be financially prohibited from acquiring a significant number of bottles, where some bottles may be used with the breast pump, some bottles may store milk in the refrigerator, and some bottles may store milk in a freezer.

Further, conventional breastmilk storage bags for storing breastmilk over a short-term or long-term period are not suitable for directly using in connection with a breast pump apparatus. The conventional breastmilk storage bag cannot attach to the breast pump apparatus when a mother is expressing milk. Thus, many mothers are forced to express milk into a breast pump bottle and then transfer the milk to a breastmilk storage bag for storage. Some amount of milk will inevitably be lost when transferring the milk from the bottle to the storage bag, and this can be a significant issue for a mother who struggles to express enough milk to meet her infant's appetite. Additionally, the process of transferring milk from a breast pump bottle to a breastmilk storage bag can result in messes and requires parents prepare a breastmilk storage bag and additionally clean and sanitize the breast pump bottle before using the bottle again.

Additionally, conventional breastmilk storage solutions do not provide a simple visual indicator of whether the breastmilk is suitable for consumption by an infant. Infants have delicate immune systems and it is imperative that an infant consumes milk that has not spoiled or been contaminated by harmful components. Breastmilk can be stored short-term in a refrigerator and may be stored relatively long-term in a very cold freezer. Breastmilk that has been left out at room temperature for a significant period should not be provided to an infant. Therefore, because breastmilk is sensitive to developing bacteria and other harmful agents, it is important for a caretaker to ensure that breastmilk is safe for consumption before providing the milk to an infant.

Applicant herein discloses methods, systems, and devices for a fluid collection receptacle for use in connection with a pumping apparatus such as a breast pump. It is an object of the disclosure to provide a convenient fluid collection receptacle that may be utilized directly with the pumping apparatus and may provide a secure and hygienic storage option for storing a food product. Another object of this disclosure is to provide a fluid collection apparatus having a dating indicator for providing a visual indication of one or more of the age of the fluid stored within the fluid collection receptacle and/or the chemical content of the fluid stored within the fluid collection receptacle. Another object of this disclosure is to provide a disposable fluid collection receptacle that may provide a convenient and easy-to-use method for a mother to collect and store breastmilk without transferring the breastmilk between one or more receptacles.

SUMMARY

Disclosed herein is a fluid collection apparatus. The fluid collection receptacle includes a rigid connector attached to the fluid collection receptacle. The rigid connector is connectable to a breast pump manifold. The fluid collection receptacle further includes a liquid tight seal in the fluid collection receptacle. The fluid collection receptacle may be constructed of a flexible plastic

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

The present disclosure extends to apparatuses, methods, and systems for a fluid collection receptacle for holding a liquid in connection with a liquid pumping apparatus such as a breast pump. More specifically, the disclosure extends to storage bags for attachment and detachment to a breast pump device that provide convenient storage of breast milk during and after pumping. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

Before the structure, systems, and methods for a liquid storage receptacle are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Reference will now be made in detail to the exemplary embodiments, examples of which are illustrated in the accompanying drawings. Wherever possible, the same reference numbers are used throughout the drawings to refer to the same or like parts. It is further noted that elements disclosed with respect to embodiments are not restricted to only those embodiments in which they are described. For example, an element described in reference to one embodiment or figure, may be alternatively included in another embodiment or figure regardless of whether or not those elements are shown or described in another embodiment or figure. In other words, elements in the figures may be interchangeable between various embodiments disclosed herein, whether shown or not.

Figure 1:
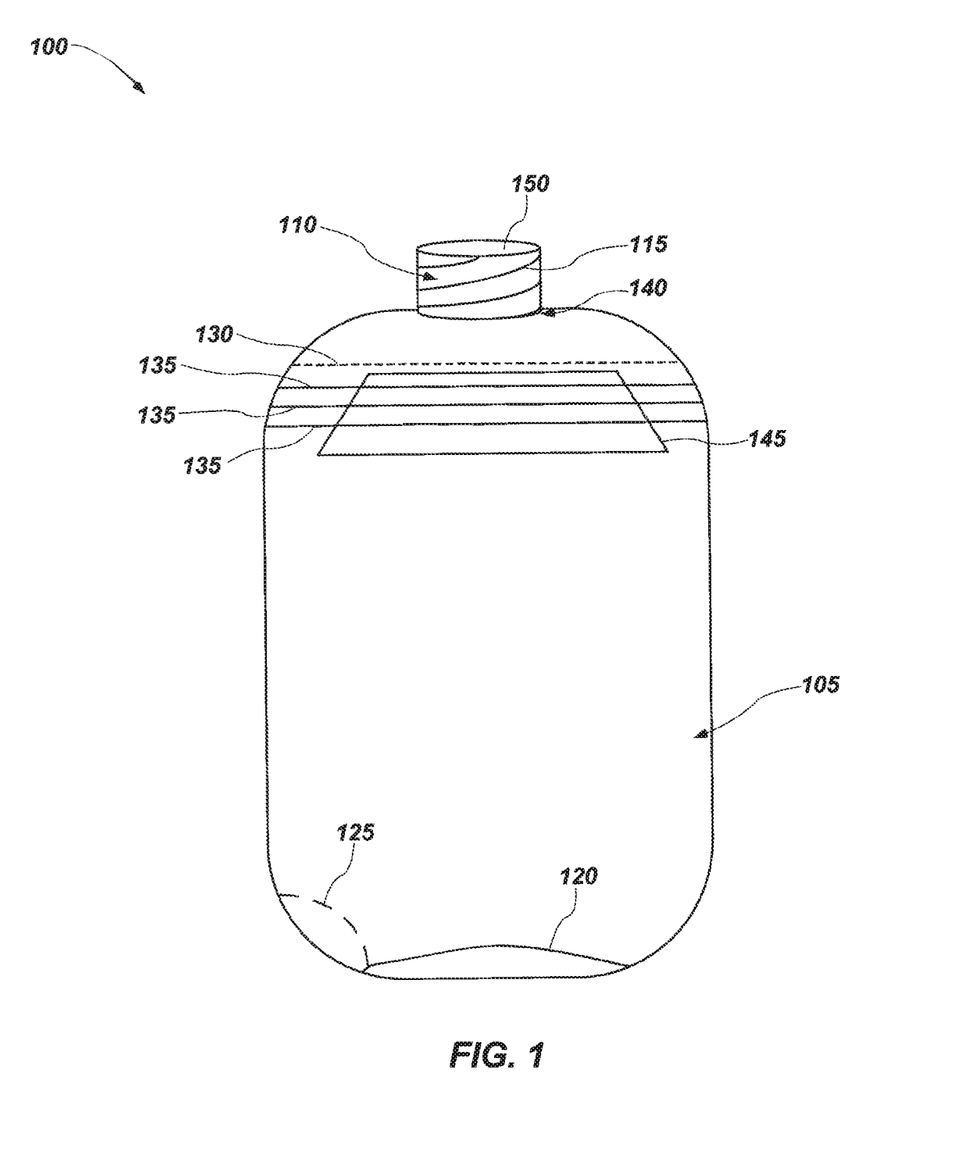
FIG. 1 illustrates a front view of a fluid collection receptacle for use in connection with a pumping apparatus in accordance with the technologies and features of the disclosure.

Referring now to the figures, FIG. 1 illustrates an embodiment of an apparatus 100 for collecting and storing a liquid. The apparatus 100 is configured for use with a liquid pumping device such as a breast pump. The apparatus 100 includes a collection receptacle 105 attached to a connector 110. Connector 110 may be constructed from a hard plastic, for example, and be affixed (bonded or welded) to collection receptacle 105. The collection receptacle 105 includes a bottom portion 120 such that the collection receptacle 105 may stand upright as illustrated in FIG. 1. The collection receptacle 105 includes drain opening 125 configured for draining any liquid that is stored in the collection receptacle 105 by tearing or cutting drain opening 125 from collection receptacle 105. The collection receptacle 105 includes one or more seals 135 which may be sealed by pressing a tongue on one of the collection receptacle 105 into a corresponding groove on an opposite side of the collection receptacle 105 (the apparatus 100 as illustrated in FIG. 1 includes three separate seals 135) and thereby be configured for sealing a liquid in the collection receptacle 105 (e.g., creating a liquid tight seal). The collection receptacle 105 includes a tear-away strip 130 configured for easily disconnecting the collection receptacle 105 from the connector 110. The connector 110 includes rigid collar 140, disposed inside connector 110 for allowing milk to pass from, for example a breast pump apparatus into the collection receptacle 105. In an embodiment, the outside of connector 110 includes one or more threads 115 that may include male or female threading configured for attaching the connector 110, and therefore collection receptacle 105, to a manifold of a breast pump apparatus.

The collection receptacle 105 may be implemented as a bag for collecting milk that is expressed by a breast pump apparatus. In various embodiments the collection receptacle 105 may be implemented as a rigid container such as a bottle or a non-rigid container such as a bag or pouch. In an embodiment, milk is collected in the collection receptacle 105 via an opening such as the interior space of the connector 110. The collection receptacle 105 may be formed of a rigid or semi-rigid plastic material, or it may alternatively be formed of a flexible plastic material. The collection receptacle 105 may be constructed of a food-grade material that is considered safe for collection of biological material such as breastmilk that may later be consumed. The collection receptacle 105 may be free of BPA (bisphenol A) and BPS (bisphenol S), which are each organic compounds commonly used during fast-drying epoxy resin adhesives and are commonly found in consumer plastics. The collection receptacle 105 may be implemented as a plastic material that is suitable for frozen storage of a fatty food such as breastmilk. In an embodiment the collection receptacle 105 is intended to replace a bottle during a breast pumping session such that a user may pump breastmilk directly into the collection receptacle 105 and then store the breastmilk within the collection receptacle 105 for a short-term or long-term period. In an embodiment the collection receptacle 105 includes gradation markings indicating an approximate volume of fluid within the bag when the collection receptacle 105 has been filled.

The apparatus 100 may include one or more sensors that may be implemented singly or in combination with an additional sensor. In an embodiment the sensor is disposed within the collection receptacle 105 or within a rigid collar 140 of the connector 110. The sensor may be configured for sensing a volume of liquid that is collected in the collection receptacle 105. In an embodiment the sensor is implemented as time-of-flight sensor for determining an amount of time between when a beam of light is emitted and when a reflection of the beam of light is detected. A computer processor associated with the sensor may determine a distance between a plurality of sensors and a volume of liquid collected within the collection receptacle 105. Accordingly, a liquid such as breastmilk collects within collection receptacle 105 and the sensor of the collection receptacle and/or connector 110 monitors a volume of rising liquid within the collection receptacle 105. For example, as breastmilk is collected during a breast pumping session, the one or more sensors may be utilized to determine a volume of breastmilk collected within the collection receptacle 105 by a computer processor associated with the one or more sensors. The computer processor may further determine a flow rate for liquid, such as breastmilk, entering the collection receptacle 105. Other types of sensors are possible, such as sensors disposed in the manifold that count uniform droplets of milk with a specific volume.

The bottom portion 120 of the collection receptacle 105 may enable the collection receptacle 105 to stand upright. In an embodiment where the collection receptacle 105 is a bag, the bottom portion 120 (e.g., a gusset) is an additional side of the bag that enables the collection receptacle 105 to stand upright without assistance particularly when there is a fluid within the collection receptacle 105. The drain opening 125 is integrated into the bottom portion 120 in an embodiment, although drain opening 125 may alternatively be located elsewhere in the collection receptacle. The drain opening 125 may include a notch or perforated portion such that the drain opening 125 is opened when a user tears or cuts away a portion of the collection receptacle 105 at the notch or perforated portion. In an alternative embodiment the drain opening 125 may include a valve, spout, or tubing connection. The drain opening 125 may be implemented as a rigid spout having a lid or cap such that the drain opening 125 may be opened on more than one occasion without rendering the collection receptacle 105 unsuitable for storing a liquid.

The seal 135 is configured for sealing the liquid within the collection receptacle 105. In an embodiment where the collection receptacle 105 is a bag, the seal 135 may include a slider seal, a channel seal, a double zipper seal, a zip-top seal, a press seal, or any other suitable seal known in the art. In an embodiment, the collection receptacle 105 includes a plurality of seals 135 to provide additional security in keeping the liquid within the collection receptacle 105. The additional seal 135 may further provide additional protection against foreign contaminants and may promote maintain a sterile or nearly sterile environment within the collection receptacle 105.

The tear-away strip 130 may be implemented as a notch or perforation within the collection receptacle 105 bag. In an embodiment where the tear-away strip 130 includes a notch, the collection receptacle 105 may be constructed of a material that will tear easily when started at the notch. In an embodiment where the tear-away strip 130 includes a perforation, the perforation may extend the width of the collection receptacle 105 and may assist a user in tearing the collection receptacle 105 along a straight line that does not interfere with a seal 135. The tear-away strip 130 is configured to enable a user to utilize the apparatus 100 with the connector 110 when expressing and collecting milk, and then remove the connector 110 from the collection receptacle 105 after expressing milk. In an embodiment the collection receptacle 105 is a bag and may be sealed along the one or more seals 135 and stored in a flat orientation when the connector 110 is removed.

The rigid collar 140 may be implemented as a rigid component configured to attach to a breast pump apparatus and configured to provide an opening wherein milk may pass to be collected in the collection receptacle 105. Rigid collar 140 may allow fluid to collect in the collection receptacle 105 and permits the connector 110 to mate with another device such as a breast pump manifold, as will be discussed below. In an embodiment the connector 110 is sized to permit a valve, which will be discussed below, to be suspended in an interior space of the collection receptacle 105. In an embodiment the connector 110 includes threads 115 or threading for securing the connector 115 to a breast pump apparatus, such as a breast pump manifold connection, as will be discussed below. The threads 115 may include female or male threading configured to match male or female threading in the breast pump component. Collection receptacle 105 may be implemented with multiple layers of flexible plastic material or may include a single layer of plastic material. Collection receptacle 105 may further include one or more tabs 145 which may be used to assist in opening collection receptacle 105, optionally by providing a user with additional leverage to separate seal 135 to allow the bag to be opened. In one embodiment, one or more tabs 145 may be implemented as two tabs 145 which are implemented on opposing sides of collection receptacle 145 or at least opposing portions of seal 135. Tabs 145 may be formed by slits in one layer of bag material, may be implemented as folds during manufacture, or may include separate elements which are permanently affixed to collection receptacle 105 during manufacture (e.g., plastic elements which are heat bonded to collection receptacle 105). Connector 110 may further be covered with a top 150 which may be implemented as a removable foil or pull tab over an opening to collection receptacle 105, or with a reusable breakaway cap, to ensure that collection receptacle 105 is sterile at the first use of collection receptacle 105, as discussed below.

Figure 2:
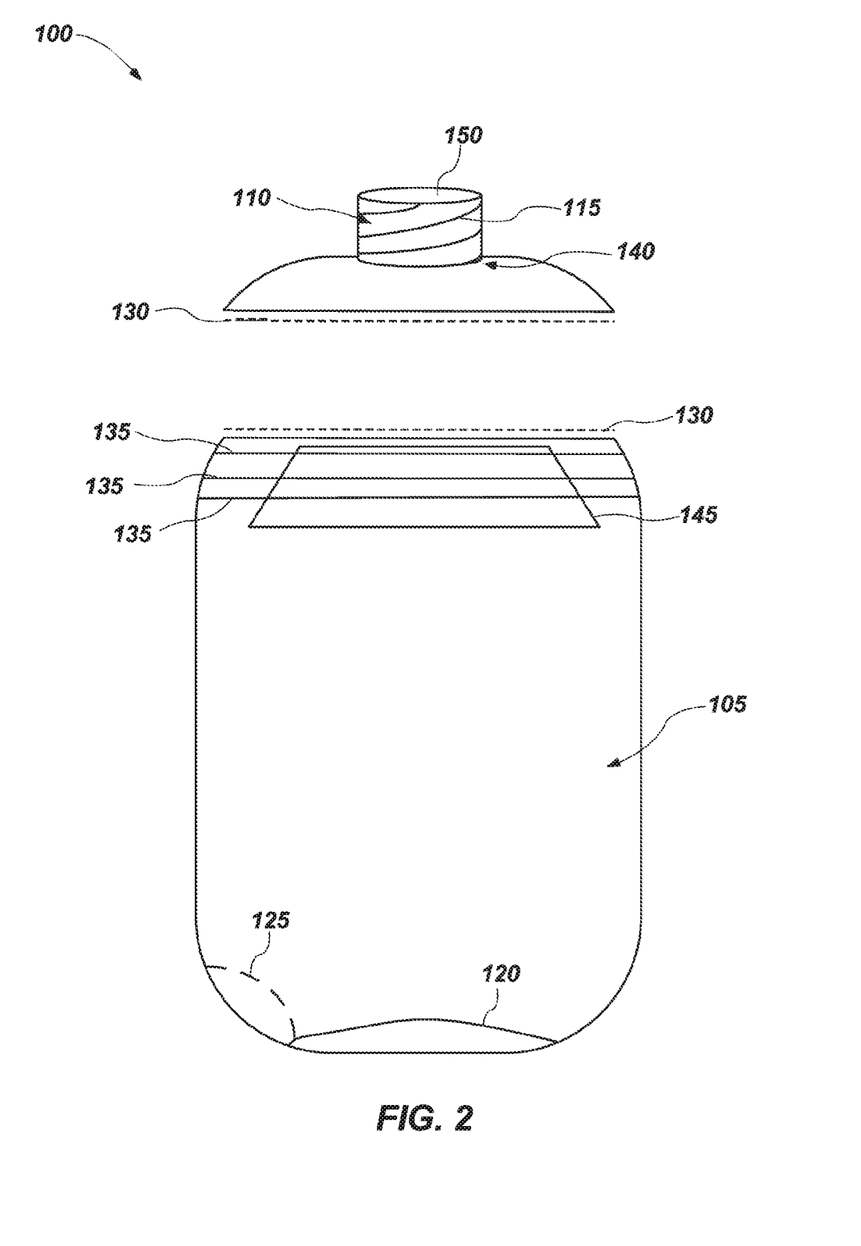
FIG. 2 illustrates a front view of a fluid collection receptacle for use in connection with a pumping apparatus in accordance with the technologies and features of the disclosure.

Referring to FIG. 2, the apparatus 100 for collecting and storing a liquid as illustrated in FIG. 1 is shown in a fragmented orientation where the connector 110 has been torn away from the collection receptacle 105 along the tear-away strip 130. A remnant of the tear-away strip 130 can be seen attached to the collection receptacle 105 and the connector 110.

Figure 3:
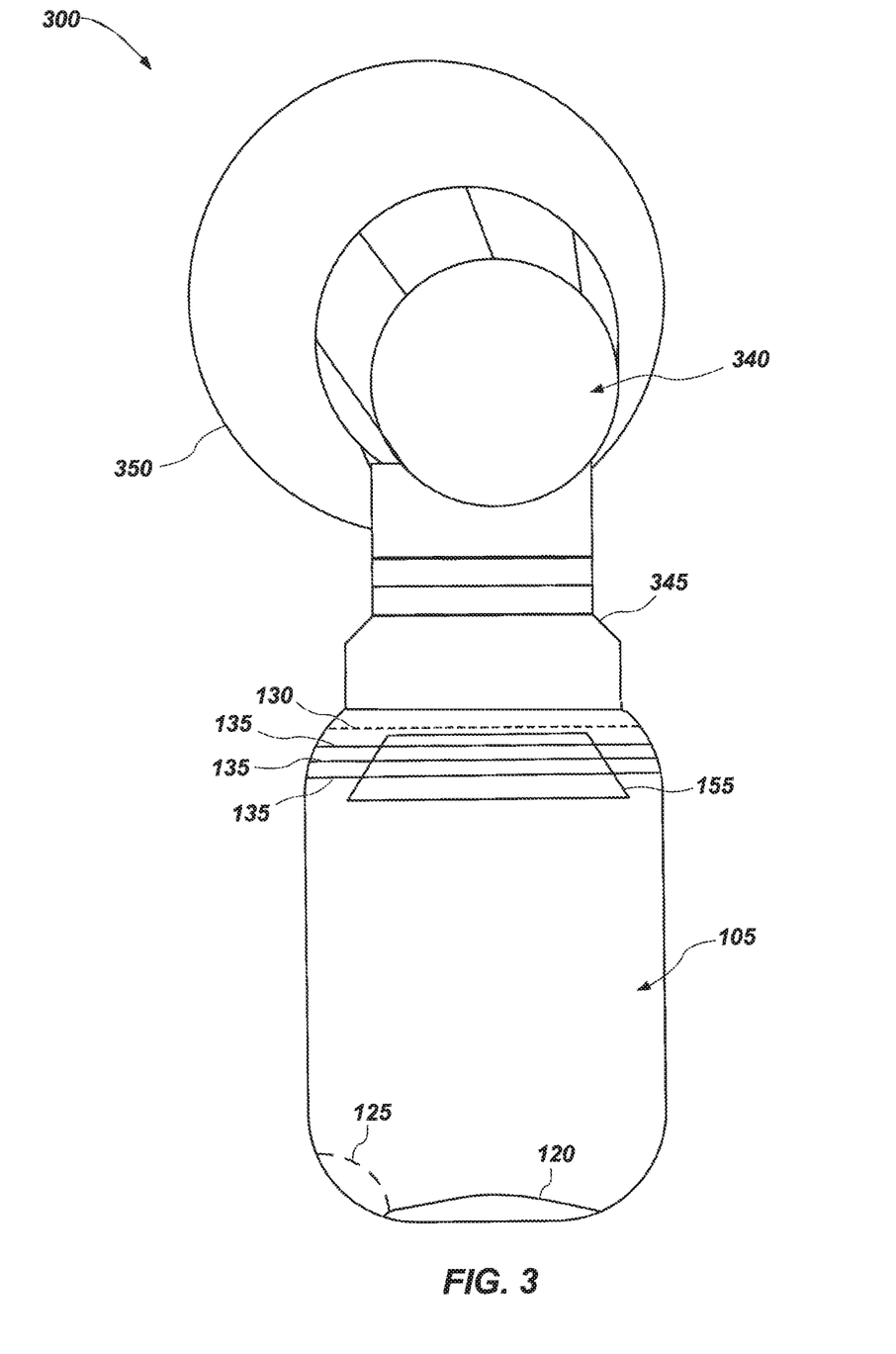
FIG. 3 illustrates a front view of a fluid collection receptacle including a manifold for use in connection with a pumping apparatus in accordance with the technologies and features of the disclosure.

FIG. 3 illustrates an apparatus 300 for collecting and storing a liquid. The apparatus 300 is configured for use with a liquid pumping device such as a breast pump that is configured for suctioning and pumping breastmilk. Like the apparatus 100 as illustrated in FIGS. 1-2, the apparatus 300 includes a collection receptacle 105 having a bottom portion 120, a drain opening 125, a plurality of seals 135, and one or more tabs 155 which may be similar in implementation to tabs 145 discussed above with respect to FIG. 1. The collection receptacle 105 further includes a tear-away strip 130 wherein the collection receptacle 105 may be removed from a manifold connection 345 that connects the collection receptacle 105 to a manifold 340 (connector 110 with rigid collar 140, shown in FIG. 1 have been threaded into manifold connection 345 of manifold 340 in FIG. 3). The manifold 340 is attached to a flange 350 that is configured to be pressed against a breast when pumping breastmilk.

The manifold 340 may include a number of elements which are not illustrated in FIG. 3, including computer hardware, one or more processors, various types of memory (static, dynamic, flash, etc.), receivers, transmitters, antennas, various sensors, a vacuum pump, and other elements that permit the breast pump to interact with, for example, a device such as a mobile phone. A vacuum pump, not illustrated, may also be a component of the breast pump and may be in fluid communication with the manifold 340 via tubing or some other connection.

In an embodiment the manifold 340 includes sensors for determining an amount of liquid that has been expressed with the breast pump and is collected in the collection receptacle 105. Such sensors may be implemented as a uniform droplet sensor configured for promoting droplets of liquid to pass from the manifold 340 in a uniform mass and/or volume, such that a total volume of liquid may be determined based on the number of uniform droplets that have passed from the manifold 340 to the collection receptacle 105.

The manifold connection 345 is connected to the manifold 340. The manifold connection 345 may house one or more valves and membranes, not illustrated, for collecting milk to be stored in the collection receptacle 105. The manifold connection 345 may be attached to the collection receptacle with threading, such as the threading that corresponds to the threads 115 illustrated in FIGS. 1-2. The manifold connection 345 may be attached to a connector 110 of the collection receptacle 105 via a compression fitting. The manifold connection 345 may be affixed to an upper portion of the collection receptacle 105 and may be disposable along with connector 110 of the collection receptacle 105. The manifold connection 345 may be affixed to the collection receptacle 105 where the manifold connection 345 is intended to be disposed of after expressing milk into the collection receptacle 105. The manifold connection 345 may be removably attached to the collection receptacle 105, for example via a connector 110, where the manifold is not intended to be disposed of after expressing milk and is instead intended to be reused and attached to a new collection receptacle 105 when expressing milk again.

The flange 350 is a component of a breast pump and is configured to contact a user's breast when the user is expressing milk with the breast pump. The flange 350 may be constructed of various sizes to accommodate different users, and the flange 350 may be removably attached to the manifold 340 via a compression fitting or other suitable connection.

In an embodiment, a valve is attached to the manifold connection 345 and the valve is suspended in the collection receptacle 105. The valve, which is discussed below, may be in fluid communication with the manifold 340 and a vacuum breast pump apparatus. The valve is configured to permit a fluid, such as breastmilk, to exit the valve when applicable and maintain a vacuum environment when a fluid is not exiting the valve to be collected in the collection receptacle 105. The manifold 340 may include a tubing connection (see e.g. 955 in FIG. 9) that is in fluid communication with a breast pump apparatus and provides a vacuum in the manifold 940 for drawing milk from a breast that is connected to the flange 350.

Figure 4:
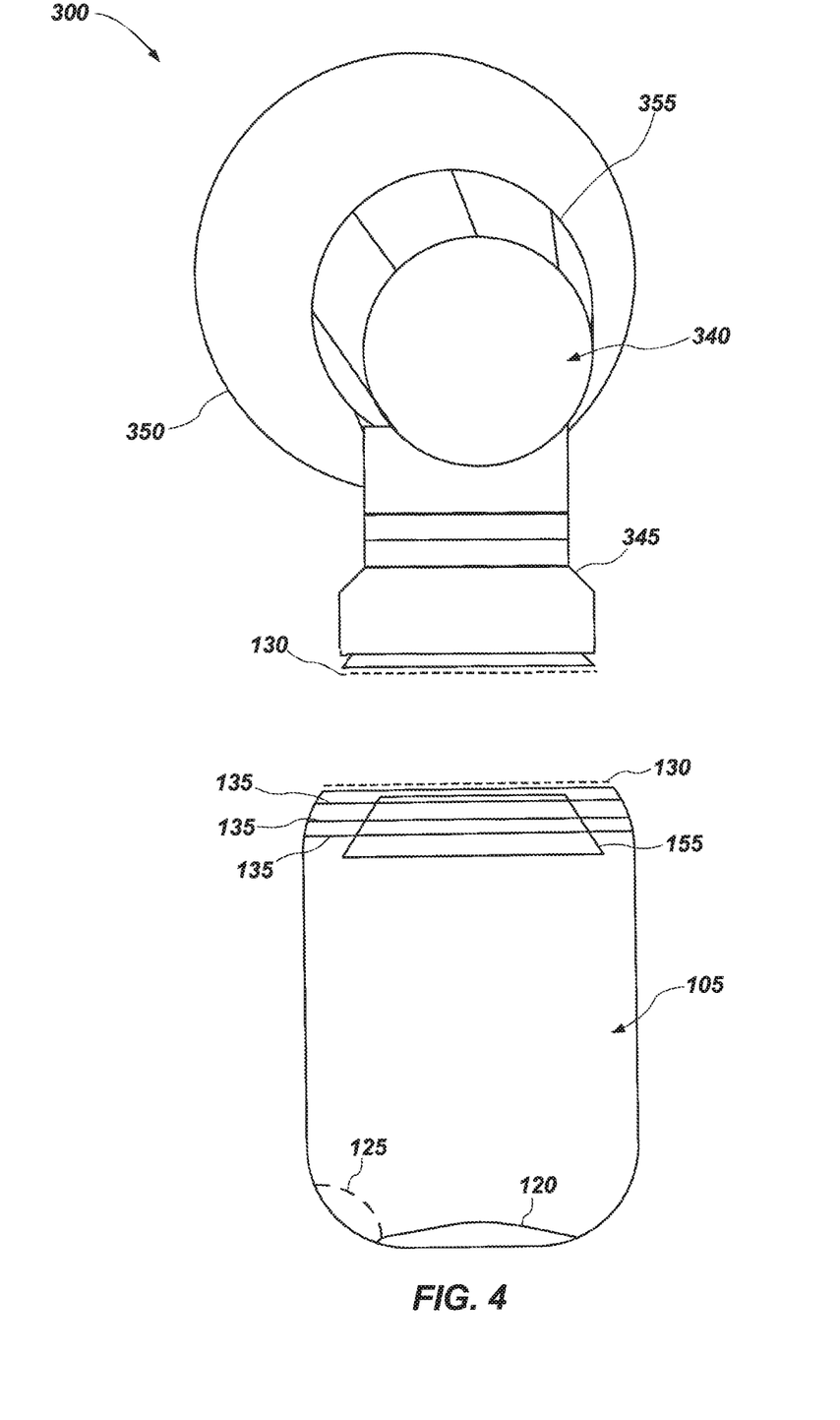
FIG. 4 illustrates a front view of a fluid collection receptacle including a manifold for use in connection with a pumping apparatus in accordance with the technologies and features of the disclosure.

Referring to FIG. 4, the apparatus 300 for collecting and storing a liquid as illustrated in FIG. 3 is shown in a fragmented orientation where the manifold 340 has been torn away from the collection receptacle 105 along the tear-away strip 130. A remnant of the tear-away strip 130 can be seen attached to the collection receptacle 105 and the manifold connection 345.

Figure 5:
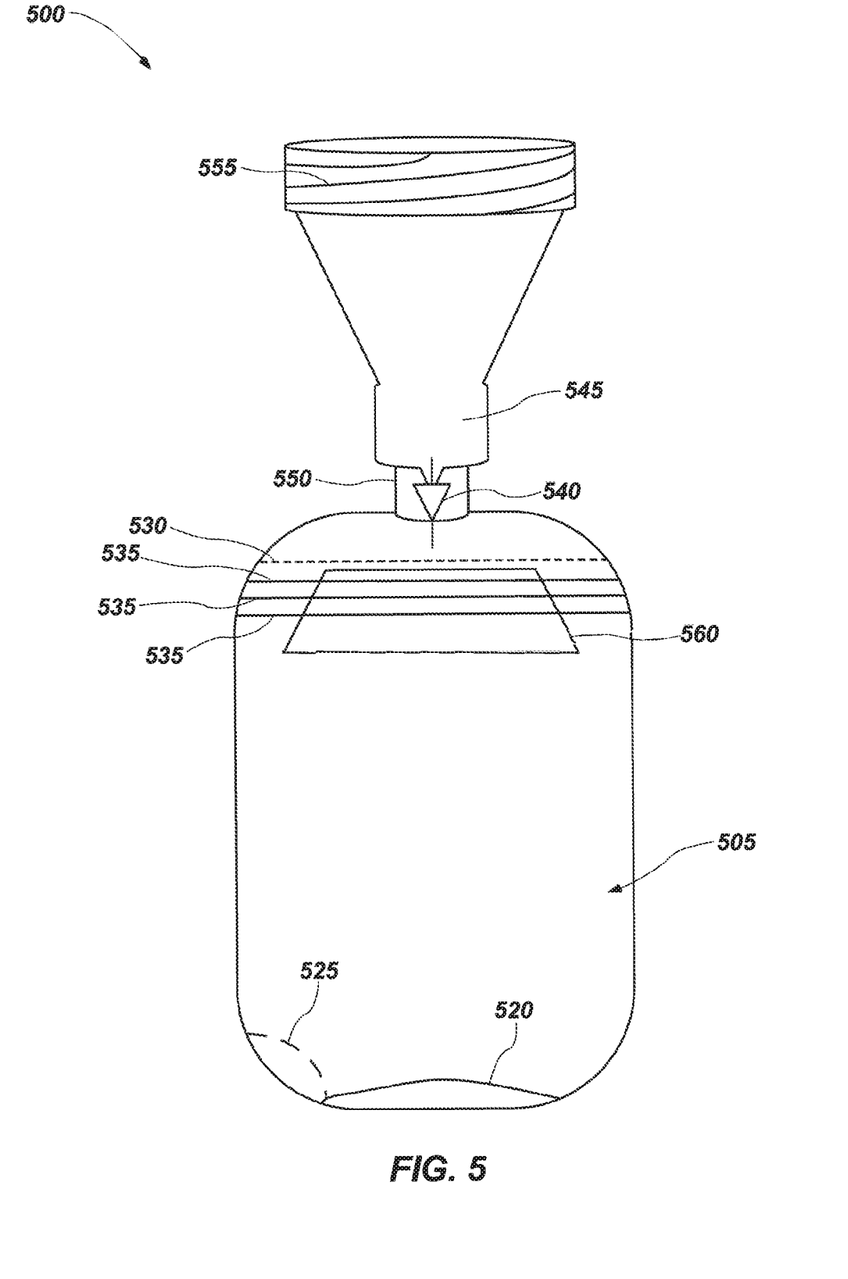
FIG. 5 illustrates a front view of a fluid collection receptacle for use in connection with a pumping apparatus in accordance with the technologies and features of the disclosure.

FIG. 5 illustrates an apparatus 500 for collecting and storing a liquid, and in one embodiment for collecting and storing breastmilk that has been expressed by a breast pump apparatus. Like apparatus 100 and apparatus 300 as illustrated in FIGS. 1-2 and 3-4, the apparatus 500 includes a collection receptacle 505 having a bottom portion 520, a drain opening 525, and one or more tabs 560. The apparatus 500 includes a manifold connection 545 having a threaded attachment component 555. The collection receptacle 505 includes a one-way valve 540 and a valve connection 550 secured to the collection receptacle distal to the bottom portion 520 such that the one-way valve 540 is removed when the tear-away strip 530 is torn.

The one-way valve 540 may be implemented as a valve affixed to the collection receptacle 505 or affixed to the manifold connection 545 such that it may be removably attached to the collection receptacle 505. The one-way valve 540 is configured to permit a liquid, such as breastmilk, to pass from the manifold connection 545 and into the collection receptacle 505. The one-way valve 540 may be defaulted to a closed position and activated only by an affirmative action by a user (e.g., applying vacuum pressure to one way valve 540), connecting the collection receptacle 505 to the manifold connection 545 or a manifold (see 340), or by activating the breast pump apparatus, for example. The one-way valve 540 may be beneficial in an embodiment where the collection receptacle 505 is utilized for collecting a biological material such as breastmilk that should be kept sterile or nearly sterile. Infant children, and particularly newborn babies, who ingest breastmilk can be particularly sensitive to outside contaminants and are benefited by ingesting breastmilk that has been maintained in a strictly hygienic environment. The one-way valve 540 is configured to provide additional protection against outside contaminants such that only breastmilk may enter the collection receptacle 505 when the breast pump is in use. In an embodiment the one-way valve 540 is configured to close automatically when the breast pump is no longer in use (e.g., vacuum pressure is released) and the collection receptacle 505 is removed from the manifold connection 545 or manifold 340. The one-way valve 540 may be implemented as a diaphragm valve, a spool valve, a plug valve, a pinch valve, a needle valve, a globe valve, a gate valve, a choke valve, a ball valve, and any other suitable valve known in the art. It should be appreciated that the structure of the one-way valve 540 may be selected according to the type of fluid to be collected in the collection receptacle 505 or the type of pump being used.

In additional embodiments, and particularly where the collection receptacle 505 is not intended to collect breastmilk, the one-way-valve 540 may instead be a multi-directional valve that permits fluid to flow in more than one direction through the valve. In an embodiment where the collection receptacle 505 is intended to collect breastmilk that is expressed by a breast pump, the one-way valve 540 may be a one-way valve that defaults to a closed position when the apparatus 500 is not in active use. In an embodiment, an interior space of the collection receptacle 505 is sterile and includes a foil cover, or a pull tab, or a cap to preserve sterility within that environment before, during, and after collection of breastmilk.

The valve connection 550 houses the one-way valve and may be affixed to the collection receptacle 505. In an embodiment, the valve connection 550 is permanently affixed to the collection receptacle 505 and is intended to be torn off along a tear-away strip (see 130) when a user has finished collecting a fluid in the collection receptacle 505, and then discarded along with the upper portion of the collection receptacle 505. In an embodiment the manifold connection 545 is connected to the collection receptacle 505 via a fitting on the valve connection 550. In an embodiment the manifold connection 545 and the valve connection 550 form a secure compression fitting. It should be appreciated that any appropriate fitting may be used, including a threaded fitting and so forth. In an embodiment, the valve connection 550 is affixed to the manifold connection 545 and the collection receptacle 505 such that the manifold connection 545 is discarded along with the upper portion of the collection receptacle 505 when a user tears the collection receptacle 505 along a tear-away strip (see 130) such as that illustrated in FIG. 1.

The manifold connection 545 is configured to provide fluid communication between a manifold 340 and the one-way valve 540 and further the collection receptacle 505. In an embodiment as illustrated in FIG. 5, the manifold 340 may be screwed onto the manifold connection 545 at the threaded attachment component 555. The threaded attachment component 555 may be configured to mate with an appropriate manifold 540 of a breast pump apparatus. In an embodiment, the manifold connection 545 is instead rigidly affixed to the manifold 540 and the manifold connection 545 is attached to the valve connection 550 or the collection receptacle 505 when a user wishes to use the breast pump. In various embodiments of the disclosure, different components, including the valve connection 550, the manifold connection 545, and the manifold 540 may be rigidly affixed to the collection receptacle 505 and may be intended to be disposable, or such components may be removably affixed to the collection receptacle 505 and may be intended to be reused.

In additional embodiments, the collection receptacle 505 includes a tear-away strip 530 where the collection receptacle 505 may be separated from the one-way valve 540 and manifold connection 545. In an embodiment as illustrated in FIG. 5, the one-way valve 540 may default to a closed position when the apparatus 500 is no longer in use and is not connected to the manifold connection 545. In such an embodiment, the one-way valve 540 may automatically provide a seal on the collection receptacle 505 and this may negate any need for a user to manually seal the collection receptacle 505 after collecting a fluid such as breastmilk. In such an embodiment the user may simply remove the manifold connection 545 from the valve connection 550 and store the collection receptacle 505 with the fluid stored therein. In an alternative embodiment, the collection receptacle 505 may further include a tear-away strip (see 130) and one or more seals (see 135).

Figure 6:
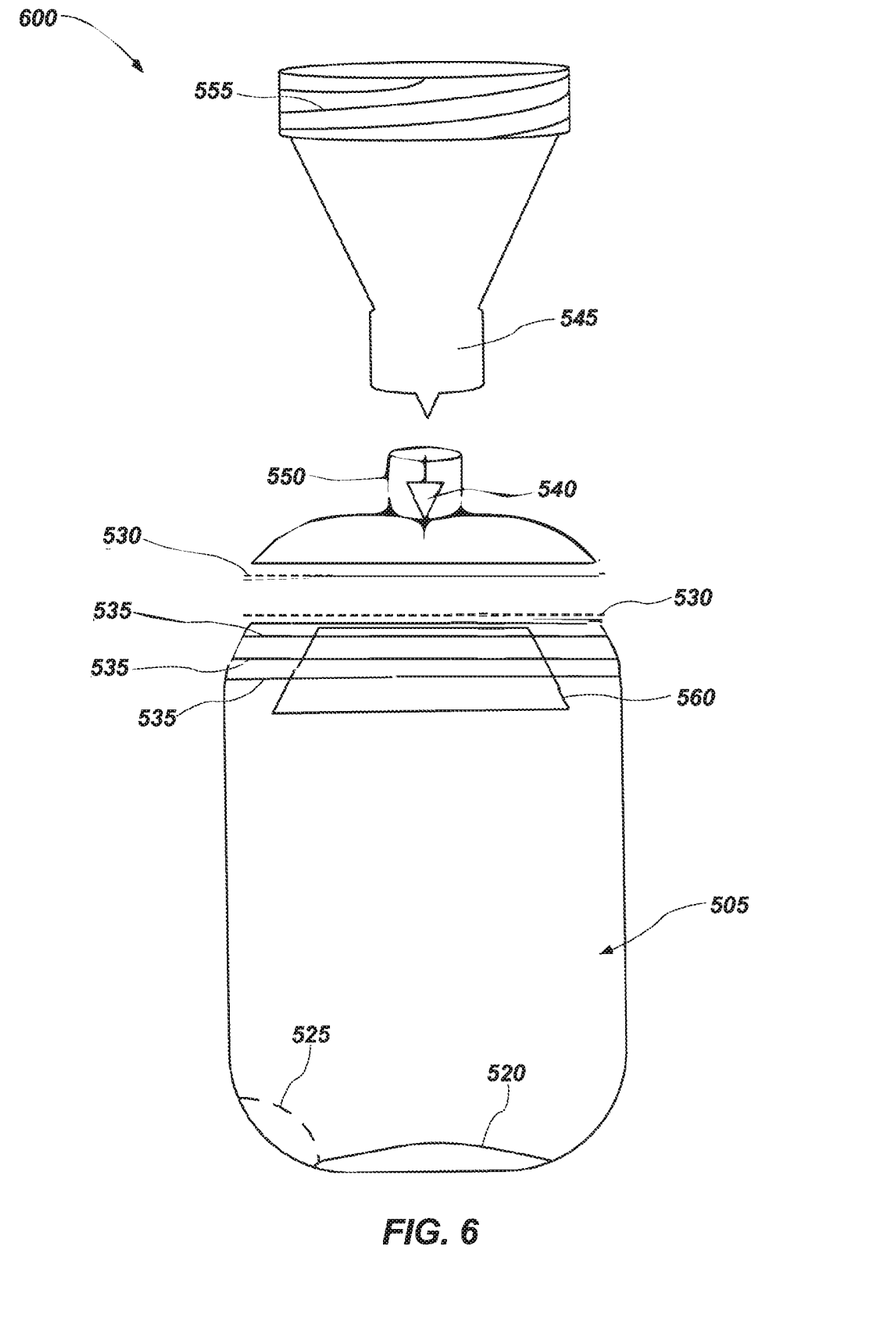
FIG. 6 illustrates a front view of a fluid collection receptacle for use in connection with a pumping apparatus in accordance with the technologies and features of the disclosure.

FIG. 6 illustrates an exploded view of an apparatus 500 that represents an alternative embodiment to the apparatus 500 illustrated in FIG. 5. The apparatus 500 is in a fragmented orientation where the portion of the collection receptacle 505 including the valve 540 and valve connection 550 has been torn away from the portion of the collection receptacle 505 that includes the bottom portion 520. The collection receptacle 505 has been torn along the tear-away strip 630 as illustrated. The collection receptacle 505 further includes a plurality of seals 535 configured for sealing the contents of the collection receptacle 505 after the valve connection 550 and the one-way valve 540 have been torn along the tear-away strip 530. In an embodiment as illustrated in FIG. 6, the manifold connection 545 has been disconnected from the valve connection 550. In an alternative embodiment, the manifold connection 545 may be affixed to the valve connection 550 and not intended to be removed. In such an embodiment, the manifold connection 545 is disposable along with the upper portion of the collection receptacle 505.

In an embodiment (see FIG. 5) the one-way valve 540 and the valve connection 550 are secured to the collection receptacle 505. In such an embodiment the valve connection 505 may be a bag and the valve connection 550 may be integrated into a plastic material of the bag. In such an embodiment the valve connection 550 and the one-way valve 540 are disposable and are intended to be discarded along with the collection receptacle 505 when a user has drained or discarded a fluid that was stored in the collection receptacle 505. In such an embodiment, the one-way valve 540 may default to a closed position when it is not in fluid communication with the breast pump apparatus via the manifold connection 545. The one-way valve 540 may thereby provide a secure and hygienic seal for the collection receptacle 505 and may negate a need for a user to manually seal the collection receptacle 505 after collecting a fluid.

In an embodiment (see FIG. 6), the valve connection 550 and the one-way valve 540 are secured to the collection receptacle 505 and are configured to be torn away along the tear-away strip 530 after a user has collected a fluid in the collection receptacle 505. In such an embodiment, the user may seal the collection receptacle 505 with the one or more seals 535 provided on the collection receptacle 505. In such an embodiment the manifold connection 545 may be affixed to the valve connection 550 or it may alternatively be removably attached to the valve connection 550 as illustrated in FIG. 6. The user may alternatively use one or more tabs 560 to open the seals when the user desires to access the fluid in collection receptacle 505.

In an embodiment (not shown), the one-way valve 540 and the valve connection 550 are secured to the manifold connection 545. In such an embodiment the valve connection 550 and the one-way valve 540 may be intended to be reused when a user wishes to utilize the breast pump again with a different collection receptacle 505. In such an embodiment, the valve connection 550 and the one-way valve 540 may be removable from the collection receptacle 505 and may be utilized again with a different collection receptacle 505.

In another embodiment (not shown), the one-way valve 540 and the valve connection 550 may be positioned at a top of manifold connection 545 such that the one-way valve 540 may be positioned such that the one-way valve 540 is planar to a top of threaded attachment component 555. Alternatively, one-way valve 540 may be disposed above threaded attachment component 555 and be fully, or at least partially disposed within a manifold of a breast pump.

In an embodiment as illustrated in FIG. 6, the manifold connection 545 can be removed from the valve connection 550. In such an embodiment, the manifold connection 545 may be utilized again and the one-way valve 540 may be discarded when the collection receptacle 505 is torn along the tear-away strip 530. Additionally, the manifold connection 545 may be configured to activate and/or open the one-way valve such that fluid may collect in the collection receptacle 505 only when the manifold connection 545 is attached to the collection receptacle 505 at the valve connection 550 or when vacuum pressure is applied to one-way valve 540. Such an embodiment may prevent contamination of the contents of the collection receptacle 505 and may promote a sterile environment within the collection receptacle 505 for storing biological materials such as breastmilk.

In an alternative embodiment, the manifold connection 545 is not removed from the valve connection 550. In such an embodiment, the manifold connection 545 is disposable along with the valve connection 550, the one-way valve 540, and the upper portion of the collection receptacle 505 that has been torn away from the lower portion of the collection receptacle 505.

Figure 7:
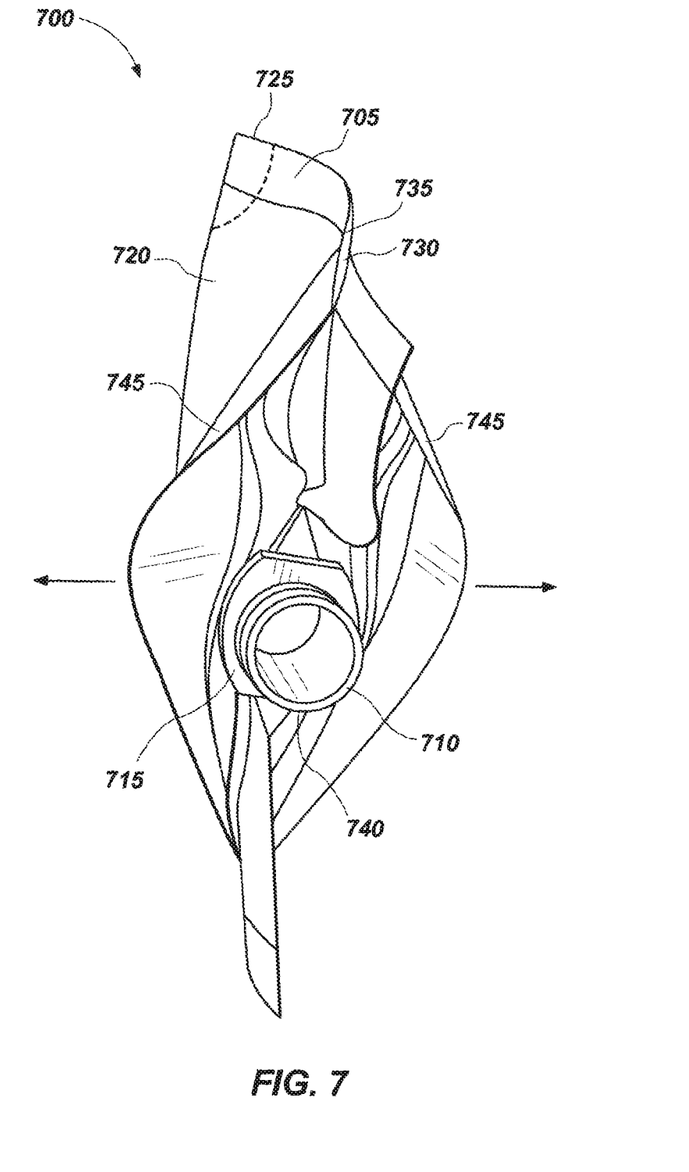
FIG. 7 illustrates a top view of the fluid collection receptacle.

FIG. 7 illustrates an embodiment of an apparatus 700 for collecting and storing a liquid. The apparatus 700 includes a collection receptacle 705 attached to a connector 710. Connector 110 may be constructed from a hard plastic, for example, and be affixed (bonded or welded) to collection receptacle 705. The welding or bonding of the connector may be hidden by the collar of the bottle. The collection receptacle 705 includes a bottom portion 720 such that the collection receptacle 705 may stand upright. The collection receptacle 705 includes drain opening 725 configured for draining any liquid that is stored in the collection receptacle 705. The collection receptacle 705 includes one or more seals 735 which may be sealed with seal 735 by pressing a tongue on one side of the collection receptacle 705 into a corresponding groove on an opposite side of the collection receptacle 705 and thereby be configured for sealing a liquid in the collection receptacle 705. The collection receptacle 705 includes a tear-away strip 730 configured for easily disconnecting the collection receptacle 705 from the connector 710. The connector 710 includes rigid collar 740, disposed inside connector 710 for allowing milk to pass from, for example a breast pump apparatus into the collection receptacle 705. In an embodiment, the an outside of connector 710 includes one or more threads 715 that may include male or female threading configured for attaching the connector 710, and therefore collection receptacle 705, to a manifold of a breast pump apparatus.

The bottom portion 720 of the collection receptacle 705 may enable the collection receptacle 705 to stand upright. In an embodiment where the collection receptacle 705 is a bag, the bottom portion 720 (e.g., a gusset) is an additional side of the bag that enables the collection receptacle 705 to stand upright without assistance particularly when there is a fluid within the collection receptacle 705. The drain opening 725 is integrated into the bottom portion 720 in an embodiment, although drain opening 725 may alternatively be located elsewhere in the collection receptacle. The drain opening 725 may include a notch or perforated portion such that the drain opening 725 is opened when a user tears away a portion of the collection receptacle 705 at the notch or perforated portion. In an alternative embodiment the drain opening 725 may include a valve, spout, or tubing connection.

Collection receptacle 705 may further include one or more tabs 745 which may be used to assist in opening collection receptacle 705, optionally by providing a user with additional leverage to separate seal 735 to allow the bag to be opened. In one embodiment, one or more tabs 745 may be implemented as two tabs 745 which are implemented on opposing sides of collection receptacle 745 or at least opposing portions of seal 735. Tabs 745 may be formed by slits in one layer of bag material, may be implemented as folds during manufacture, or may include separate elements which are permanently affixed to collection receptacle 705 during manufacture (e.g., plastic elements which are heat bonded to collection receptacle 705).

Figure 8:
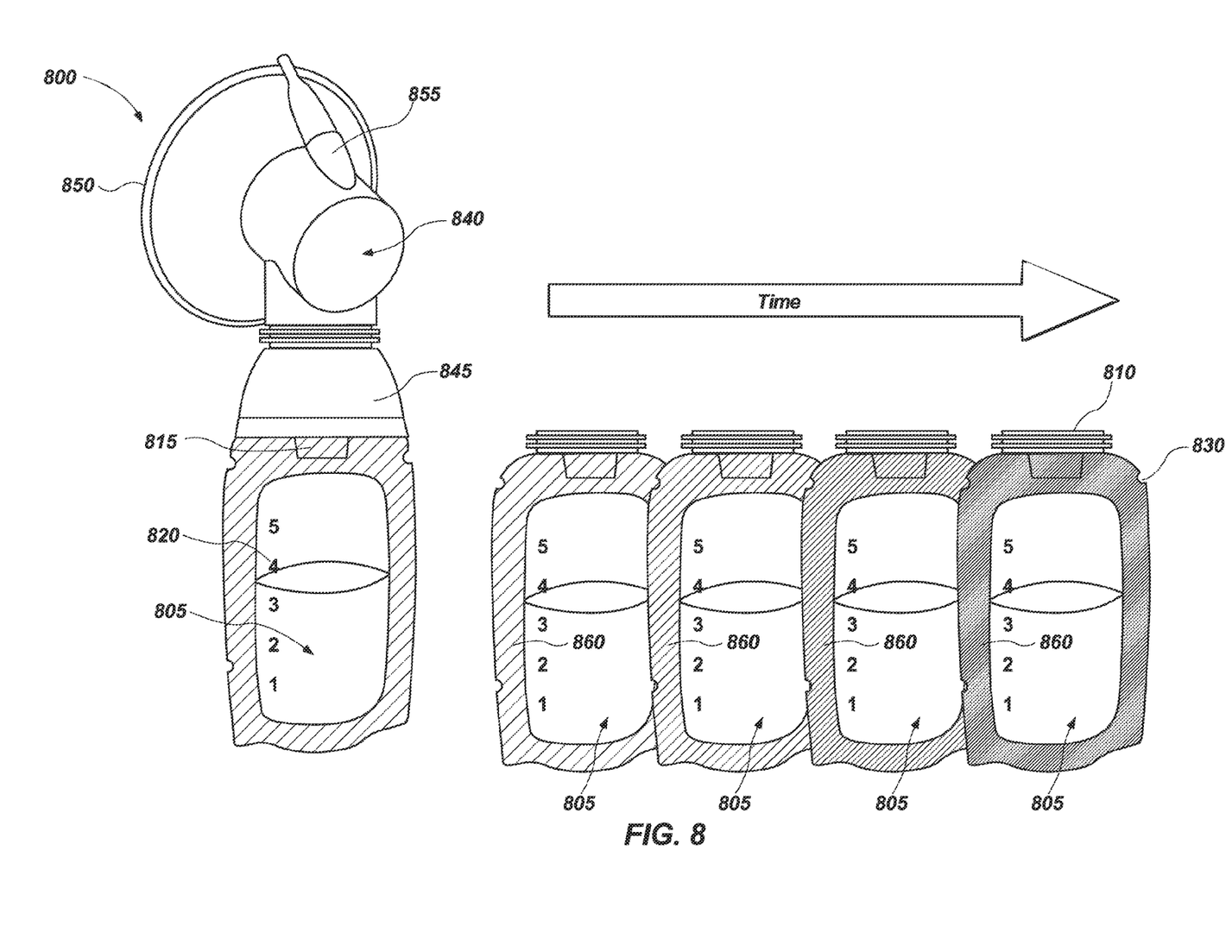
FIG. 8 illustrates a plurality of fluid collection receptacles having a dating indicator for use in connection with a pumping apparatus in accordance with the technologies and features of the disclosure.

FIG. 8 illustrates an image of an apparatus 800 for collecting and storing a liquid. The apparatus 800 is configured to be in fluid communication with a breast pump for expressing breastmilk. The apparatus 800 includes a collection receptacle 805. A plurality of collection receptacles 805 are illustrated in FIG. 8, with one collection receptacle 805 attached to a manifold 840 of a breast pump. The collection receptacle 805 includes a tear-away strip 830 configured for enabling a user to remove an upper portion of the collection receptacle 805 away from a lower portion of the collection receptacle 805. The collection receptacle includes a rigid connection 810 attached to an upper portion of the collection receptacle 805. The rigid connection 810 is configured to attach to a manifold connection 845, and the manifold connection is secured to the manifold 840 of the breast pump. In an embodiment the manifold 840 is connected to a flange 850 of a breast pump. The manifold 840 is in fluid communication with a vacuum tubing 855 that is in communication with a vacuum pump of a breast pump. In an embodiment, a valve 815 is attached to and in fluid communication with the manifold 840, and the valve 815 is suspended in an interior space of the collection receptacle 805. In an embodiment, the collection receptacle 805 includes a plurality of markings 820 for indicating a volume of liquid within the collection receptacle 805. In an embodiment, the collection receptacle 805 includes a dating indicator 860 for providing a visual indication of an approximate age of the liquid.

The tear-away strip 830 may be implemented as a notch as illustrated in FIG. 8 or it may alternatively be implemented as a perforated strip. It should be appreciated that the tear-away strip 830 may be implemented as any suitable mechanism for enabling a user to easily separate a top portion of the collection receptacle 805 away from a bottom portion of the collection receptacle 805.

The dating indicator 860 may be implemented as a film on an interior or exterior surface of the collection receptacle 805 that is configured to indicate an approximate age of the contents of the collection receptacle 805 or the collection receptacle 805 itself. In an embodiment the dating indicator 860 is configured to change colors as the dating indicator 860 is exposed to oxygen or other environmental components, or when it is exposed to cold temperatures such as when the collection receptacle 805 is stored in a freezer. In an embodiment the dating indictor 860 is a color changing plastic material and may comprise the entire collection receptacle 805 or it may comprise only portions, such as the outer edges as shown in FIG. 8, of the collection receptacle 805.

The dating indicator 860 may be implemented as a time-temperature indicator. A time-temperature indicator is capable of showing a time-temperature-dependent relationship as an irreversible color change. In an embodiment the time-temperature indicator is a film affixed to an interior or exterior surface of the collection receptacle 805. A user may be advised to not utilize breastmilk stored within the collection receptacle 805 if the dating indicator 860 has undergone a color change. The time-temperature indicator may be configured to undergo a gradual color change upon accumulated temperature exposure and may give a user an idea of the freshness of the breastmilk stored within the collection receptacle 805.

The dating indicator 860 may be implemented as an oxygen-sensitive indicator. An oxygen-sensitive indicator may include components sensitive to oxidation that may change color over time as the dating indicator 860 is exposed to the environment. The oxygen-sensitive indicator may be disposed on an interior surface of the collection receptacle 805 such that the dating indicator 860 begins to gradually change color only after the collection receptacle 805 has been opened for a first time and utilized.

The dating indicator 860 may be implemented as an indicator placed inside the sealed collection receptacle 805. The dating indicator 860 may be designed to alert a user of a chemical change occurring within the contents of the collection receptacle 805. Such a dating indicator 860 may be sensitive to a specific by-product that originates from deterioration reactions in food such as breastmilk.

The dating indicator 860 may be implemented as an electrochromic polymer capable of undergoing reversible changes in its optical absorption properties when ions are inserted electrochemically into its crystal structure. An example of an electrochromic polymer may include a conjugated polymer where the polymer may change color when impacted by an external stimulus capable of changing the nature of an energy gap between molecules in the conjugated polymer's orbitals.

The dating indicator 860 may be implemented as a polymer opal film including crystals constructed of repeating units that have a large contrast in optical properties. The range of frequencies causes variations in the light that is reflected in certain regions of the film and can enable the film to exhibit a color. The appearance of the color may be influenced by changes in the manner in which the crystals are arranged and placement of nanoparticles within the film.

The valve 815 is a component of the breast pump apparatus and may be suspended in the collection receptacle 805 in an embodiment as illustrated in FIG. 8. The valve is configured to maintain a vacuum created within components of the manifold connection 845 and the manifold 840.

The foregoing description has been presented for purposes of illustration. It is not exhaustive and does not limit the invention to the precise forms or embodiments disclosed. Modifications and adaptations will be apparent to those skilled in the art from consideration of the specification and practice of the disclosed embodiments. For example, components described herein may be removed and other components added without departing from the scope or spirit of the embodiments disclosed herein or the appended claims.

Other embodiments will be apparent to those skilled in the art from consideration of the specification and practice of the disclosure disclosed herein. It is intended that the specification and examples be considered as exemplary only, with a true scope and spirit of the invention being indicated by the following claims.

What is claimed is:

1. A fluid collection receptacle, comprising:
   a rigid connector directly attached to the fluid collection receptacle as a part of the fluid collection receptacle which is connectable to a breast pump manifold; and
   a liquid tight seal in the fluid collection receptacle, wherein the liquid tight seal seals the fluid collection receptacle while the fluid collection receptacle is connected to the breast pump manifold,
   wherein the fluid collection receptacle is constructed of a flexible plastic, and includes a dating indicator, the dating indicator providing a visual indication of an age of a liquid in the fluid collection receptacle, and the visual indication being a color of the fluid collection receptacle.

2. The fluid collection receptacle of claim 1, further comprising: a tear-away strip disposed between the rigid connector and the liquid tight seal.

3. The fluid collection receptacle of claim 1, further comprising a drain.

4. The fluid collection receptacle of claim 3, wherein the drain is disposed at a bottom portion of the fluid collection receptacle.

5. The fluid collection receptacle of claim 4, wherein the drain is a tear away or cut-away drain.

6. The fluid collection receptacle of claim 1, further comprising: a gusset at a bottom portion of the fluid collection receptacle such that the fluid collection receptacle stands upright when a fluid is stored therein.

7. The fluid collection receptacle of claim 1, further comprising a one-way valve attached to the fluid collection receptacle.

8. The fluid collection receptacle of claim 7, wherein the one-way valve permits a fluid to collect in the fluid collection receptacle.

9. The fluid collection receptacle of claim 1, wherein the connector includes a foil cover over an opening in the connector.

10. The fluid collection receptacle of claim 1, wherein the connector includes a cap over an opening in the connector.

11. The fluid collection receptacle of claim 10, wherein the connector includes a removable pull tab over the opening of the connector.

12. The fluid collection receptacle of claim 1, further comprising a tab.

13. The fluid collection receptacle of claim 12, further comprising a second tab.

14. The fluid collection receptacle of claim 13, wherein the tab and the second tab are disposed on opposing sides of the fluid collection receptacle.

15. The fluid collection receptacle of claim 1, wherein the connector that is connectable to the breast pump manifold is further connected to the fluid collection receptacle.

16. The fluid collection receptacle of claim 1, wherein the fluid collection receptacle further includes a spout which mates with the connector.

17. The fluid collection receptacle of claim 1, wherein the connector includes threads that mate with the breast pump manifold.

\* \* \* \* \*